United States Patent
Zuniga et al.

(10) Patent No.: US 11,459,527 B2
(45) Date of Patent: Oct. 4, 2022

(54) CLEANSING COMPOSITIONS AND USE THEREOF

(71) Applicant: Colgate-Palmolive Company, New York, NY (US)

(72) Inventors: Arturo Zuniga, Del Miguel Hidalgo (MX); Claudia Bentosa, Del Azcapozalco (MX); Henry Pena, Edo México (MX)

(73) Assignee: Colgate-Palmolive Company, New York, NY (US)

( * ) Notice: Subject to any disclaimer, the term of this patent is extended or adjusted under 35 U.S.C. 154(b) by 143 days.

(21) Appl. No.: 16/767,187

(22) PCT Filed: Nov. 30, 2017

(86) PCT No.: PCT/US2017/063930
§ 371 (c)(1),
(2) Date: May 27, 2020

(87) PCT Pub. No.: WO2019/108198
PCT Pub. Date: Jun. 6, 2019

(65) Prior Publication Data
US 2020/0392427 A1    Dec. 17, 2020

(51) Int. Cl.
| | | |
|---|---|---|
| *C11D 1/00* | (2006.01) | |
| *C11D 1/83* | (2006.01) | |
| *A61K 8/04* | (2006.01) | |
| *A61K 8/34* | (2006.01) | |
| *A61K 8/42* | (2006.01) | |
| *A61K 8/46* | (2006.01) | |
| *A61K 8/81* | (2006.01) | |
| *A61K 8/86* | (2006.01) | |
| *A61Q 19/10* | (2006.01) | |
| *C11D 3/00* | (2006.01) | |
| *C11D 3/37* | (2006.01) | |
| *C11D 11/00* | (2006.01) | |
| *C11D 1/12* | (2006.01) | |
| *C11D 1/75* | (2006.01) | |

(52) U.S. Cl.
CPC ................ *C11D 1/83* (2013.01); *A61K 8/046* (2013.01); *A61K 8/345* (2013.01); *A61K 8/42* (2013.01); *A61K 8/463* (2013.01); *A61K 8/8147* (2013.01); *A61K 8/86* (2013.01); *A61Q 19/10* (2013.01); *C11D 3/0026* (2013.01); *C11D 3/3707* (2013.01); *C11D 3/3765* (2013.01); *C11D 11/0023* (2013.01); *C11D 1/12* (2013.01); *C11D 1/75* (2013.01)

(58) Field of Classification Search
CPC .......... C11D 1/83; C11D 3/3707; A61K 8/463
See application file for complete search history.

(56) References Cited

U.S. PATENT DOCUMENTS

| | | |
|---|---|---|
| 6,180,587 B1 | 1/2001 | Fuller et al. |
| 7,928,053 B2 | 4/2011 | Hecht et al. |
| 2005/0143269 A1 | 6/2005 | Wei et al. |
| 2007/0009463 A1 | 1/2007 | Niebauer et al. |
| 2007/0286832 A1 | 12/2007 | Clapp et al. |
| 2008/0019928 A1 | 1/2008 | Baecker et al. |
| 2011/0117225 A1* | 5/2011 | Wei .................. A61Q 19/10 424/757 |
| 2015/0224047 A1* | 8/2015 | Hardy .................. A61K 8/86 510/131 |
| 2018/0125771 A1 | 5/2018 | Myers |

FOREIGN PATENT DOCUMENTS

| | | |
|---|---|---|
| CN | 1377403 | 10/2002 |
| CN | 1469731 | 1/2004 |
| CN | 1193087 | 3/2005 |
| CN | 1897909 | 1/2007 |
| CN | 101048124 | 10/2007 |
| CN | 101217929 | 7/2008 |
| CN | 103040632 | 4/2013 |
| CN | 109922777 | 6/2019 |
| DE | 19915837 | 10/2000 |
| WO | 2000/61716 | 10/2000 |
| WO | 2013/016030 | 1/2013 |
| WO | 2018/089322 | 5/2018 |

OTHER PUBLICATIONS

International Search Report and Written Opinion of the International Searching Authority in International Application No. PCT/US2017/063930, dated Jun. 13, 2018.

* cited by examiner

*Primary Examiner* — Necholus Ogden, Jr.

(57) ABSTRACT

A cleansing composition comprising an aqueous solution of an anionic polymer, a nonionic polymer and a system of surfactants. Solutions as described herein comprise two distinct aqueous phases having different compositions and density. Further methods of use are also disclosed.

17 Claims, No Drawings

CLEANSING COMPOSITIONS AND USE THEREOF

BACKGROUND

Cleansing compositions are generally delivered in single phase compositions or in the form of an oil dispersed throughout an aqueous medium. However, there are significant advantages to having two or more phases present in a single container during non-use. These phases can be appealing to the eye depending upon various agents; particularly coloring agents dispersed therein or particles present at the interface of the phases. A small amount of shaking by the user prior to end use can create mixing of the phases and at times a bubbly-type appearance. There are also other benefits also associated with multi-phase compositions. For example, these compositions present an ability to simultaneously display multiple benefits, and can be advertised as serving several purposes at once. They can also drive a desired consumer appeal and formulate with reactive and/or previously thought incompatible ingredients.

Foam persistence in the presence of increasing amounts of removed soils throughout the washing session is arguably the most important cleaning efficacy signal relied on by consumers. The hand dishwashing detergent industry uses the laboratory Miniplate Test as the key laboratory appraisal method for assessing this most important performance criterion and to quantify the performance quality of liquid hand dishwashing detergent formulations.

Thus, there is a need for a cleansing composition comprising distinct aqueous phases capable of robust cleaning, prolonged stability, and having improved foaming conditions.

BRIEF SUMMARY

Provided herein are cleansing compositions comprising distinct aqueous phases capable of robust cleaning, prolonged stability, and having improved foaming conditions.

In certain embodiments, the formulations can form an unusual, aqueous biphasic system, where a hygroscopic anionic polymer is concentrated in one phase, and a nonionic polymer is concentrated in another phase. These formulations differ from conventional biphasic formulations in that both phases are aqueous, rather than one phase being hydrophobic and the other hydrophilic. They also differ from structured compositions such as gels insofar as they separate into phases having different compositions and densities, e.g., an upper phase and a lower phase, which can be readily mixed by shaking and which will then re-separate over a short period.

The disclosure thus provides, in one embodiment, a cleansing composition comprising:
  a. an acidic polymer, for example a polymer selected from one or more of (a) acrylate homopolymers or co-polymers of a combination of acrylic acid derivatives (e.g., acrylic acid, methacrylic acid, ethyl acrylate, methyl methacrylate, chloroethyl vinyl ether, butyl acrylate, 2-ethylhexyl acrylate, and salts and esters thereof), and (b) synthetic anionic linear polycarboxy-lates, such as 1:4 to 4:1 copolymers of maleic anhydride or acid with another polymerizable ethylenically unsaturated monomer, e.g., co-polymers of methyl vinyl ether/maleic anhydride, wherein some or all of the anhydride moieties are hydrolyzed to provide free carboxyl groups;
  b. a nonionic polymer; for example selected from one or more poly(alkylene oxide) polymers, e.g., selected from polyethylene glycols, polypropylene glycols, poloxamers and mixtures thereof; e.g., wherein the orally acceptable nonionic polymer has a molecular weight of at least 3000D, e.g., 6 kD to 250 kD, e.g., 8 kD;
  c. a phase-stabilizing amount of surfactants comprising a combination of at least one anionic surfactant and at least one nonionic surfactant, wherein the anionic surfactant comprises a hydrophobic group that is a $C_8$-$C_{22}$ alkyl or acyl and a water-solubilizing group selected from sulfonate, sulfate, and carboxylate (e.g., alkyl sulfates, e.g., sodium laurel ether sulfate (SLES), sodium lauryl sulfate, and ammonium lauryl sulfate), and wherein the nonionic surfactant comprises one or more aliphatic compounds (e.g., amine oxides, e.g. laurylamidopropyl dimethylamine oxide, myristylamidopropyl dimethylamine oxide, and mixtures thereof), wherein the solution comprises two distinct aqueous phases having different composition and density, the two distinct phases comprising substantially all of one of the anionic polymer or the nonionic polymer.

The disclosure further provides methods of using such compositions, for example, cleaning hard surfaces or cleaning skin.

DETAILED DESCRIPTION

Unless otherwise specified, all percentages and amounts expressed herein and elsewhere in the specification should be understood to refer to percentages by weight. Also, the term "about," when used in reference to a range of values, should be understood to refer to either value in the range, or to both values in the range. As used throughout, ranges are used as shorthand for describing each and every value that is within the range. Any value within the range can be selected as the terminus of the range.

Unless otherwise specified, all percentages and amounts expressed herein and elsewhere in the specification should be understood to refer to percentages by weight. The amounts given are based on the active weight of the material.

The present disclosure provides personal care compositions comprising a polyacrylate polymer added to a cationic and nonionic surfactant system having a low pH. In various embodiments, the polyacrylate polymer comprises polyacrylate-1 crosspolymer. The inventors have surprisingly found that in concentrations between about 1 wt % and about 7 wt %, polyacrylate-1 crosspolymer unexpectedly increases the foam profile of a cationic and nonionic surfactant system and provides the system with the ability to suspend particles for prolonged periods of time.

In one exemplary embodiment, A cleansing composition comprising an aqueous solution of:
  an acidic polymer;
  a nonionic polymer; and
  a phase-stabilizing amount of surfactants comprising a combination of at least one anionic surfactant and at least one nonionic surfactant,
  wherein the solution comprises two distinct aqueous phases having different composition and density, the two distinct phases comprising substantially all of one of the anionic polymer or the nonionic polymer.

The present disclosure provides additional exemplary embodiments, including:

1.1 Composition 1, wherein the anionic surfactant comprises a hydrophobic group that is a C8-C22 alkyl or acyl and a water-solubilizing group selected from sulfonate, sulfate, and carboxylate 1.2 Composition 1 or 1.1, wherein the anionic surfactant is an alkyl sulfate or an alkyl sulfonate.

1.3 Any of the preceding compositions, wherein the anionic surfactant is sodium laurel ether sulfate, sodium lauryl sulfate, ammonium lauryl sulfate, a sodium alkyl benzene sulfonate, or magnesium alkyl benzene sulfonate.

1.4 Any of the preceding compositions, wherein the anionic surfactant is sodium lauryl ether sulfate.

1.5 Any of the preceding compositions, wherein the anionic surfactant is present in an amount of about 5-25 wt. %, about 8-20 wt. %, about 10-18 wt. %, or about 12-16 wt. %.

1.6 Any of the preceding compositions, wherein the nonionic surfactant comprises a $C_8$-$C_{22}$ tertiary amine oxide, a fatty acid amide or an alkyl polyglucoside.

1.7 Any of the preceding compositions, wherein the nonionic surfactant comprises at least one of laurylamidopropyl amine oxide, myristylamidopropyl amine oxide, cocomonoethanolamide, or combinations thereof.

1.8 Any of the preceding compositions, wherein the nonionic surfactant comprises at least one of laurylamidopropyl amine oxide and myristylamidopropyl amine oxide.

1.9 Any of the preceding compositions, wherein the nonionic surfactant comprises a combination of laurylamidopropyl amine oxide, myristylamidopropyl amine oxide.

1.10 Any of the preceding compositions, wherein the nonionic surfactant is present in an amount of about 0.1-15 wt. %, 5-12 wt. %, or 6-9 wt. %.

1.11 Any of the preceding compositions, wherein the ratio of anionic surfactant to nonionic surfactant is about 1:4 to about 4:1, 1:3 to about 3:1, about 2:1 to about 1:2, about 1:1 to about 4:1, about 1:1 to about 1:3.5, about 1:1 to about 2.3:1, about 1.2:1 to about 2.0:1, about 1.4:1 to about 1.9:1, or about 1.5:1 to about 1.7:1.

1.12 Any of the preceding compositions, wherein the ratio of anionic surfactant to nonionic surfactant is about 1:1, about 1.1:1, about 1.2:1, about 1.3:1, about 1.4:1, about 1.5:1, about 1.6:1, about 1.7:1, about 1.8:1, about 1.9:1, about 2:1, or about 1.65:1.

1.13 Any of the preceding compositions, wherein the acidic polymer is selected from a polyacrylate made of homopolymers or co-polymers of a combination of acrylic acid derivatives (e.g., acrylic acid, methacrylic acid, ethyl acrylate, methyl methacrylate, chloroethyl vinyl ether, butyl acrylate, 2-ethylhexyl acrylate, and salts and esters thereof) or a synthetic anionic linear polycarboxylate.

1.14 Any of the preceding compositions, wherein the acidic polymer is a polyacrylate made of homopolymers or co-polymers of a combination of acrylic acid derivatives (e.g., acrylic acid, methacrylic acid, ethyl acrylate, methyl methacrylate, chloroethyl vinyl ether, butyl acrylate, 2-ethylhexyl acrylate, and salts and esters thereof).

1.15 Any of the preceding compositions, wherein the acidic polymer is a crosslinked polyacrylic acid.

1.16 Any of the preceding compositions, wherein the acidic polymer is a homopolymer of polyacrylic acid.

1.17 Any of the preceding compositions wherein the acidic polymer is selected from 1:4 to 4:1 copolymers of maleic anhydride or acid with another polymerizable ethylenically unsaturated monomer, e.g., co-polymers of methyl vinyl ether/maleic anhydride, wherein some or all of the anhydride moieties are hydrolyzed to provide free carboxyl groups.

1.18 Any of the preceding compositions wherein the acidic polymer comprises 0.01 to 30 weight % synthetic anionic linear polycarboxylate, e.g., 0.1 to 30 weight % synthetic anionic linear polycarboxylate, e.g., 1 to 30 weight % synthetic anionic linear polycarboxylate, e.g., 5 to 30 weight % synthetic anionic linear polycarboxylate, e.g., 10 to 30 weight % synthetic anionic linear polycarboxylate, e.g., 10 to 20 weight % synthetic anionic linear polycarboxylate, e.g., 15 weight % synthetic anionic linear polycarboxylate, e.g., 17 weight % synthetic anionic linear polycarboxylate.

1.19 Any of the preceding compositions wherein the acidic polymer comprises a copolymer of maleic anhydride and methyl vinyl ether.

1.20 Any of the preceding compositions wherein the acidic polymer comprises a 1:4 to 4:1 copolymer of methyl vinyl ether/maleic anhydride (optionally fully or partially hydrolyzed following co-polymerization to provide the corresponding acid).

1.21 Any of the preceding compositions wherein the acidic polymer comprises a 1:4 to 4:1 copolymer of methyl vinyl ether/maleic anhydride (optionally fully or partially hydrolyzed following co-polymerization to provide the corresponding acid) having a molecular weight (M. W.) of about 30,000 to about 1,000,000, e.g. about 300,000 to about 800,000.

1.22 Any of the preceding compositions, wherein the acidic polymer is present in an amount of about 5-25 wt. %, about 8-22 wt. %, about 10-20 wt. %, about 13-18 wt. %, about 15-17 wt. %, or about 16 wt. %.

1.23 Any of the preceding compositions wherein the nonionic polymer is selected from one or more poly(alkylene oxide) polymers.

1.24 Any of the preceding compositions wherein the nonionic polymer is selected from polyethylene glycols, polypropylene glycols, poloxamers, co-polymers of polyethylene glycol and polypropylene glycol, and mixtures thereof.

1.25 Any of the preceding compositions wherein the nonionic polymer has a molecular weight of at least 3000D, e.g., 6 kD to 250 kD.

1.26 Any of the preceding compositions wherein the nonionic polymer comprises polyethylene glycol of MW 5 kDa-35 kDa, in an amount of 1% to 10%.

1.27 Any of the preceding compositions wherein the nonionic polymer is 1-10% polyethylene glycol having a molecular weight of 5 kD to 10 kD (e.g., 8 kD).

1.28 Any of the preceding compositions, wherein the nonionic polymer is present in an amount of about 0.1-10 wt. %, 2-8 wt. %, 4-6 wt. %, or about 5 wt. %.

1.29 Any of the preceding compositions wherein the ratio of acidic polymer to nonionic polymer is about 1:1 to about 5:1, about 3:1 to about 4:1, or about 16:5.

1.30 Any of the preceding compositions wherein the composition further comprises a cationic active agent, e.g., a cationic antimicrobial agent.

1.31 Any of the preceding compositions wherein the composition further comprises a cationic active agent, which is an antimicrobial agent, in an antimicrobially effective concentration.

1.32 Any of the preceding compositions wherein the composition comprises a cationic active agent selected from one or more of quaternary ammonium surfactants (such as cetyl pyridinium chloride (CPC), benzalkonium chloride, cetyl trimethylammonium bromide or chloride, didecyldimethylammonium chloride, benzethonium chloride), bisguanides (such as chlorhexidine digluconate), cationic amino acids (such as arginine), metal cations (such as zinc, calcium, or stannous ions), or combinations thereof, e.g.

1.33 Any of the preceding compositions wherein the composition is a personal or home care product, e.g., a skin or hard surface cleanser, and comprises an effective amount of a cationic active which is an antimicrobial cationic surfactant, selected from antimicrobial quaternary ammonium cations (e.g. benzalkonium chloride, cetyl trimethylammonium bromide or chloride, didecyldimethylammonium chloride, cetylpyridinium chloride, benzethonium chloride) and antimicrobial bisguanides (e.g., chlorhexidine digluconate), and combinations thereof.

1.34 Any of the preceding compositions further comprising a zwitterionic surfactant that is a quaternary ammonium carboxylate betaine.

1.35 Any of the preceding compositions further comprising a zwitterionic surfactant selected from cocoamidopropyl betaine and laurylamidopropyl betaine.

1.36 Any of the preceding compositions, wherein composition is in the form of a liquid hand soap, shampoo, conditioner, liquid face soap, dish soap, antiperspirant, deodorant, body wash, dermal lotion, dermal cream, dermal conditioner, or liquid detergent.

1.37 Any of the preceding compositions, wherein the composition further comprises one or more ingredients selected from among:
 (a) Humectants (e.g., glycerin, sorbitol, propylene glycol),
 (b) Fatty acids (e.g., caproic acid, caprylic acid, capric acid, lauric acid, myristic acid, palmitic acid, palmitoleic acid, stearic acid, oleic acid, linolenic acid, linoleic acid, arachidic acid, arachidonic acid),
 (c) Fatty alcohols (e.g., cetearyl alcohol, cetyl alcohol, stearyl alcohol, oleyl alcohol),
 (d) Esters of fatty acids (e.g., esters of caproic acid, caprylic acid, capric acid, lauric acid, myristic acid, palmitic acid, palmitoleic acid, stearic acid, oleic acid, linolenic acid, linoleic acid, arachidic acid, arachidonic acid, with alcohols such as glycerol, propylene glycol, sorbitan, isopropyl alcohol, caproic alcohol, capryl alcohol, capric alcohol, lauryl alcohol, myristyl alcohol, cetearyl alcohol, cetyl alcohol, palmoleyl alcohol, stearyl alcohol, oleyl alcohol, linoyl alcohol, linolenyl alcohol, arachidyl alcohol, arachidonyl alcohol) such as isopropyl myristate, capryl stearate, isopropyl olivate, cetearyl olivate, cetearyl oleate, glyceryl caprylate, glyceryl stearate citrate, and sorbitan olivate), natural and synthetic triglycerides (e.g., di- or tri-glycerides of fatty acids, such as glyceryl caprate or caprylic/capric triglyceride),
 (e) Waxes (e.g., cetearyl wax, beeswax, carnauba wax, lanolin wax, candelilla wax, and paraffin wax),
 (f) Thickeners (e.g., silicas, xanthan gum, guar gum, agar, alginates, carrageenan, gellan gum, pectins, and modified cellulose polymers, such as hydroxycellulose, hydroxypropyl cellulose, hydroxyethyl cellulose, hydroxybutyl cellulose, hydropropyl methylcellulose, hydroxyethyl propyl cellulose),
 (g) Emulsifiers (e.g. polyethylene glycol esters, fatty alcohol polyglycol ethers, fatty acid polyglycol ethers, polyglycerol fatty acid esters, sorbitol, sorbitan, and mono- and di-fatty acid esters of sorbitan),
 (h) Sunscreen actives (e.g., titanium dioxide, zinc oxide, and UV absorption inhibitors, such as octyl methoxy cinnamate, benzophenone-3, and methylene bis-benzotriazolyl tetramethyl butyl phenol),
 (i) Vitamins (e.g., vitamin A, vitamin E, esters of vitamin A or vitamin E, such as vitamin E acetate and retinyl palmitate).

1.38 Any of the preceding compositions, further comprising inorganic salts, brighteners, perfumes, colorants, sequestering agents, opacifiers, pearlizers, chelating agents (e.g., EDTA), or any combination thereof 1.39 Any of the preceding compositions, wherein the composition is a cosmetic product, cosmetic-removal product, deodorant or antiperspirant product, hair care product, shaving product (e.g., creams, gels and foams), sun bathing product (e.g., sunscreen compositions and tanning compositions), insect repellent product, skin care product or personal cleansing product (e.g., liquid soaps, foams, gels, and lotions), a liquid hand soap, shower gel, body wash, bath foam, shampoo, liquid face soap, dish soap, body wash, dermal cream, or liquid laundry detergent, or liquid detergent for cleaning hard surfaces.

1.40 Any of the preceding compositions, wherein the composition is a cream, lotion or gel for the skin (e.g., face, hands, feet, etc.).

1.41 Any of the preceding compositions, wherein the composition is a liquid hand soap, dish soap, liquid laundry detergent, or liquid detergent for cleaning hard surfaces.

1.42 Any of the preceding compositions, further comprising natural biological extracts, such as essential oils or fragrances (e.g., Amyris oil, cedarwood oil, cocoa absolute, copaiba balsam, menthe oil pays, myrrh resin, patchouli oil, vanillin, vetiver oil, Aloe extract, lemon extract, orange extract, mandarin extract, and oil or extract of anise, clove, basil, aniseed, cinnamon, geranium, rose, mint, lavender, thyme, rosemary, citronella, cypress, eucalyptus, peppermint, and sandalwood).

1.43 Any of the preceding compositions, comprising:
 a) an acidic polymer, for example a polymer selected from one or more of (a) acrylate homopolymers or co-polymers of a combination of acrylic acid derivatives (e.g., acrylic acid, methacrylic acid, ethyl acrylate, methyl methacrylate, chloroethyl vinyl ether, butyl acrylate, 2-ethylhexyl acrylate, and salts and esters thereof), and (b) synthetic anionic linear polycarboxylates, such as 1:4 to 4:1 copolymers of maleic anhydride or acid with another polymerizable ethylenically unsaturated monomer, e.g., co-polymers of methyl vinyl ether/maleic anhydride, wherein some or all of the anhydride moieties are hydrolyzed to provide free carboxyl groups;
 b) a nonionic polymer; for example selected from one or more poly(alkylene oxide) polymers, e.g., selected from polyethylene glycols, polypropylene glycols, poloxamers and mixtures thereof; e.g., wherein the orally acceptable nonionic polymer has a molecular weight of at least 3000D, e.g., 6 kD to 250 kD, e.g., 8 kD;
 c) a phase-stabilizing amount of surfactants comprising a combination of at least one anionic surfactant and at least one nonionic surfactant, wherein the anionic surfactant comprises a hydrophobic group that is a $C_8$-$C_{22}$ alkyl or acyl and a water-solubilizing group selected from sulfonate, sulfate, and carboxylate (e.g., alkyl sulfates, e.g., sodium laurel ether sulfate (SLES), sodium lauryl sulfate, and ammonium lauryl sulfate), and wherein the nonionic surfactant comprises one or more aliphatic compounds (e.g., amine oxides, e.g.

laurylamidopropyl dimethylamine oxide, myristylamidopropyl dimethylamine oxide, and mixtures thereof), wherein the solution comprises two distinct aqueous phases having different composition and density, the two distinct phases comprising substantially all of one of the anionic polymer or the nonionic polymer.

1.44 Any of the preceding compositions, further comprising water, e.g., from 5-90% water by weight of the composition, for example, 10%-80%, 15%-80%, 20%-80%, 25%-80%, 25%-75%, 30%-75%, 30%-80%, 40%-80%, 40%-70%, 50%-75%, 50%-70%, 50%-65%, or 60%-70%, or 65-70%, or about 65%, or about 66%, or about 67%, or about 68%.

In some embodiments, the cleansing compositions of the present disclosure include a stabilizing amount of a surfactant system that is preferably comprised of an anionic surfactant and a nonionic surfactant. In some embodiments, the surfactant system comprises about 10 wt % to about 35 wt %, about 15 wt % to about 30 wt %, or about 17 wt % to about 26 wt % of the composition.

Suitable anionic surfactants include, but are not limited to, those surface-active or detergent compounds that contain an organic hydrophobic group containing generally 8 to 26 carbon atoms or generally 10 to 18 carbon atoms in their molecular structure and at least one water-solubilizing group selected from sulfonate, sulfate, and carboxylate so as to form a water-soluble detergent. Usually, the hydrophobic group will comprise a $C_8$-$C_{22}$ alkyl, or acyl group. Such surfactants are employed in the form of water-soluble salts and the salt-forming cation usually is selected from sodium, potassium, ammonium, magnesium and mono-, di- or tri-$C_2$-$C_3$ alkanolammonium, with the sodium, magnesium and ammonium cations again being the usual ones chosen.

Some examples of suitable anionic surfactants include, but are not limited to, the sodium, potassium, ammonium, and ethanolammonium salts of linear $C_8$-$C_{18}$ alkyl ether sulfates, ether sulfates, and salts thereof. Suitable anionic ether sulfates have the formula $R(OC_2H_4)_n$ $OSO_3M$ wherein n is 1 to 12, or 1 to 5, and R is an alkyl, alkylaryl, acyl, or alkenyl group having 8 to 18 carbon atoms, for example, an alkyl group of $C_{12}$-$C_{14}$ or $C_{12}$-$C_{16}$, and M is a solubilizing cation selected from sodium, potassium, ammonium, magnesium and mono-, di- and triethanol ammonium ions. Exemplary alkyl ether sulfates contain 12 to 15 carbon atoms in the alkyl groups thereof, e.g., sodium laureth (2 EO) sulfate. Some preferred exemplary anionic surfactants that may be used in the compositions of the present disclosure include sodium laurel ether sulfate (SLES), sodium lauryl sulfate, and ammonium lauryl sulfate.

Preferably, the present compositions comprise a single anionic surfactant. In some embodiments, the anionic surfactant is present in an amount of about 0.01 wt % to about 30 wt %, about 5 wt % to about 20 wt %, about 10 wt % to about 25 wt %, about 10 wt % to about 20 wt %, about 11 wt % to about 18 wt %, about 12 wt % to about 17 wt %, or about 12 wt %, or about 13 wt. %, or about 14 wt. %, or about 15 wt. %, or about 16 wt %.

The composition also comprises a nonionic surfactant. Nonionic surfactants that can be used in the compositions can broadly be defined as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name PLURONIC®), polyoxyethylene, polyoxyethylene sorbitan esters (sold under trade name TWEENS®), Polyoxyl 40 hydrogenated castor oil, fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, alkyl polyglycosides (for example, fatty alcohol ethers of polyglycosides, such as fatty alcohol ethers of polyglucosides, e.g., decyl, lauryl, capryl, caprylyl, myristyl, stearyl and other ethers of glucose and polyglucoside polymers, including mixed ethers such as capryl/caprylyl (C8-10) glucoside, coco (C8-16) glucoside, and lauryl (C12-16) glucoside), long chain tertiary amine oxides, long chain tertiary phosphine oxides, long chain dialkyl sulfoxides, and mixtures of such materials.

In some embodiments, the nonionic surfactant comprises amine oxides, fatty acid amides, ethoxylated fatty alcohols, block copolymers of polyethylene glycol and polypropylene glycol, glycerol alkyl esters, polyoxyethytene glycol octylphenol ethers, sorbitan alkyl esters, polyoxyethylene glycol sorbitan alkyl esters, and mixtures thereof. Examples of amine oxides include, but are not limited to, laurylamidopropyl dimethylamine oxide, myristylamidopropyl dimethylamine oxide, and mixtures thereof. Examples of fatty acid amides include, but are not limited to, cocomonoethanolatnide, lauramide monoethanolamide, cocodiethanolamide, and mixtures thereof. In certain embodiments, the nonionic surfactant is a combination of an amine oxide and a fatty acid amide. In certain embodiments, the amine oxide is a mixture of laurylamidopropyl dimethylamine oxide and myristylamidopropyl dimethylamine oxide. In certain embodiments, the nonionic surfactant is a combination of lauryl/myristylamidopropyl dimethylamine oxide and cocomonoethanolamide. In certain embodiments, the nonionic surfactant is present in an amount of about 0.1 to about 20 wt % of the composition. In other embodiments, the amount is about 0.1 to about 10, about 0.1 to about 6.0, about 0.5 to about 10, about 0.5 to about 5, or about 0.5 to about 3 wt %.

In some embodiments, the cleansing compositions of the present disclosure includes an acidic polymer. In some embodiments, the acidic polymer is made of acrylate (interchangeably referred to herein as acrylic acid) homopolymers or co-polymers of a combination of acrylic acid derivatives. For example, the polymer may be a chain of one or more monomers selected from acrylic acid, methacrylic acid, alkyl methacrylates, ethyl acrylate, methyl methacrylate, chloroethyl vinyl ether, butyl acrylate, 2-ethylhexyl acrylate, and salts and esters thereof. In various embodiments, the acrylate polymer may be crosslinked with an allyl ether pentaerythritol, an allyl ether of sucrose, an allyl ether of propylene; polyhaloalkanols such as 1,3-dichloroisopropanol, 1,3-dibromoisopropanol; sulfonium zwitterions such as the tetrahydrothiophene adduct of novolac resins; haloepoxyalkanes such as epichlorohydrin, epibromohydrin, 2-methyl epichlorohydrin and epiiodohydrin; polyglycidyl ethers such as glycerine diglycidyl ether, ethylene glycol diglycidyl ether, propylene glycol diglycidyl ether, diethylene glycol diglycidyl ether; and the mixtures thereof. For example, the acidic polymer may be obtained as Accusol 445/445N/445ND sold by The DOW Chemical Company in Basking Ridge, N.J.

In other embodiments, the acidic polymer may include one or more carboxy groups, for example selected from one or more of synthetic anionic linear polycarboxylates. The appropriate molecular weight will vary depending on the specific polymer, the degree of crosslinking or branching, and the proportion of acidic functional groups, but in general, the molecular weight is greater than 5000 g/mol. In various embodiments, the acidic polymer could be in a linear or nonlinear (i.e. branched) form or a mixture of linear and branched forms, the backbone or side chains could contain various hydrophobic moieties such as methyl methacrylate monomers, alkane chains, etc., and/or as hydrophilic uncharged moieties such as PEG or PPG, as well as moieties bearing acidic functional groups. Examples of acidic polymers include synthetic anionic linear polycarboxylatesand can be selected from a variety of anionic polymers backbones including vinyl, acrylic, maleic. Carboxylate moieties along the polymer backbone can come from the monomers themselves, such as in the case of acrylic acid, methacrylic acid, or maleic acid, or can be generated from the hydrolysis of the polymer, such as in the case of poly-butyl acrylate. The acidic polymer can be made up of copolymers or homopolymers of acidic functional monomers or mixtures thereof.

In some embodiments, "synthetic anionic linear polycarboxylate" refers to 1:4 to 4:1 copolymers of maleic anhydride or acid with another polymerizable ethylenically unsaturated monomer, e.g., methyl vinyl ether (methoxyethylene), having a molecular weight (M. W.) of about 30,000 to about 2,500,000; for example 1:4 to 4:1, e.g. about 1:1, copolymers of methyl vinyl ether/maleic anhydride, wherein the anhydride is hydrolyzed following co-polymerization to provide the corresponding acid, having a molecular weight (M. W.) of about 30,000 to about 1,000,000, e.g. about 300,000 to about 800,000, e.g., as sold under the trade name GANTREZ®, e.g., GANTREZ® S-97 Pharmaceutical Grade (M. W. ca. 700,000), available from Ashland Specialty Chemicals, Bound Brook, N.J. 08805.

In various embodiments, the composition further includes a nonionic polymer.

The nonionic polymer is a water soluble polymer which does not form an ionic species at relevant pH, e.g., between pH 3 and 10, for example in certain embodiments selected from one or more poly(alkylene oxide) polymers, e.g., selected from polyethylene glycols (PEG), polypropylene glycols (PPG), poloxamers (block co-polymers of PEG and PPG), random copolymers of PEG and PPG, and mixtures thereof. In some embodiments, the nonionic polymer has a molecular weight of at least 3000D, e.g., 6 kDa to 250 kDa. The molecular weight may vary depending on the particular type of polymer, the degree of branching, if any, and the concentration used. Experiments with PEG having molecular weight between 6 kDa and 35 kDa, for example, showed that at lower concentrations, e.g., for a 3% concentration in a particular combination with other ingredients, a higher molecular weight material, e.g. 35 kDa, was needed to form the biphasic system, but at formulations having higher levels of PEG, a PEG having a lower molecular weight, e.g., 6 kDa could support a biphasic system. In particular embodiments, the nonionic polymer comprises a mixture of (i) polyethylene glycol (MW 5 kDa-35 kDa) and (ii) poloxamer (i.e., an ethylene oxide/propylene oxide block copolymer), e.g., poloxamer 407, which is a triblock copolymer consisting of a central hydrophobic block of polypropylene glycol flanked by two hydrophilic blocks of polyethylene glycol, wherein the approximate length of the two PEG blocks is about 101 repeat units while the approximate length of the propylene glycol block is about 56 repeat units, available commercially for example as Pluronic F127 (BASF).

In some embodiments, the composition comprises at least one structuring agent. The structuring agent may be added to compositions in the form of aqueous solutions, dispersions or emulsions. The structuring agent increases the viscosity of the composition. In various embodiments, the structuring agent is compatible with surfactant systems having both cationic and nonionic surfactants. Examples of such agents include various acrylate based thickening agents, natural or synthetic gums, polysaccharides, and the like, including but not limited to those set forth below. In some preferred embodiments, the structuring agent comprises polyacrylate-1 crosspolymer. Polyacrylate-1 crosspolymer is sold under the tradename Carbopol© Aqua-CC from Lubrizol Advanced Materials, Inc. In one aspect, the structuring agent is a copolymer of one or more C1-C5 alkyl esters of (meth)acrylic acid, C1-C4 dialkylamino C1-C6 alkyl methacrylate, PEG/PPG-30/5 allyl ether, PEG 20-25 C10-C30 alkyl ether methacrylate, hydroxy C2-C6 alkyl methacrylate cross-linked with ethylene glycol dimethacrylate.

In some embodiments, the compositions also comprise pH modifying agents, which may include acidifying agents to lower pH, basifying agents to raise pH and buffering agents to control pH within a desired range. For example, one or more compounds selected from acidifying, basifying and buffering agents can be included to provide a pH of 2 to 10, or in various illustrative embodiments 2 to 8, 3 to 9, 4 to 8, 5 to 7, 6 to 10, 7 to 9, etc. In preferred embodiments, the pH is between about 1 to 5, about 2 to 5, about 4 to 5, or about 4.2-4.8. Examples of pH modifying agent include sodium chloride, HCl, phosphoric and sulfonic acids and carboxylic acids such as lactic acid and citric acid, acid salts (e.g., monosodium citrate, disodium citrate, monosodium malate, etc.), alkali metal hydroxides such as sodium hydroxide and potassium hydroxide, carbonates such as sodium carbonate, bicarbonates, sesquicarbonates, borates, silicates, phosphates (e.g., monosodium phosphate, trisodium phosphate, pyrophosphate salts, etc.), imidazole and the like. One or more pH modifying agents are optionally present in a total amount effective to maintain the composition in an acceptable pH range.

In some embodiments, the personal care compositions of the present disclosure include a zwitterionic surfactant. Suitable zwitterionic surfactants include betaines and sultaines. In some embodiments, the zwitterionic surfactant comprises a betaine having a quaternary ammonium or phosphonium ion as the cationic group and a carboxylate group as the anionic group; for comprises a betaine having a quaternary ammonium ion as the cationic group and a carboxylate group as the anionic group (i.e., a quaternary ammonium carboxylate betaine). Typical alkyldimethyl betaines include, but are not limited to, decyl dimethyl betaine or 2-(N-decyl-N, N-dimethylammonia)acetate, coco dimethyl betaine or 2-(N-coco N, N-dimethylammonia) acetate, myristyl dimethyl betaine, palmityl dimethyl betaine, lauryl dimethyl betaine, cetyl dimethyl betaine, stearyl dimethyl betaine, etc. The amidobetaines similarly include, but are not limited to, cocoamidoethylbetaine, cocoamidopropyl betaine and the like. The amidosulfobetaines include, but are not limited to, cocoamidoethylsulfobetaine, cocoamidopropyl sulfobetaine and the like.

In certain embodiments, the personal care composition is in the form of a cleansing liquid. In some embodiments, the cleansing liquid includes one or more fatty acid soaps. The fatty acid soap can be any neutralized fatty acid. Typical fatty acids used for soaps include, myristic acid, lauric acid, palmitic acid, stearic acids, and other fatty acids. Sources of fatty acids include coconut oil, palm oil, palm kernel oil, tallow, avocado, canola, corn, cottonseed, olive, hi-oleic sunflower, mid-oleic sunflower, sunflower, palm stearin, palm kernel olein, safflower, and babassu oils. The fatty acids can be neutralized with any base to form a soap. Typical bases include, but are not limited to, sodium hydroxide, potassium hydroxide, and triethanolamine. In some embodiments, the soap is a potassium soap. In some embodiments, the soap is a soap of lauric acid, myristic acid, and optionally a mixture of C12-18 fatty acids.

Illustrative examples of emulsifying agents include ethoxylated carboxylic acids, ethoxylated glycerides, glycol esters, monoglycerides, polyglyceryl esters, polyhydric alcohol esters and ethers, sorbitan/sorbitol esters, triesters of phosphoric acid, and ethoxylated fatty alcohols. Examples includes glyceryl stearate, PEG-100 stearate, sorbitan stearate, PEG-40 stearate, polysorbate-20, polysorbate-60, polysorbate-80, and glyceryl oleate.

In some embodiments, personal care compositions of the present disclosure further comprise one or more ingredients selected from coloring agents, fragrances, moisturizing agents, and amino acids.

In some embodiments, personal care compositions of the present disclosure comprise at least one viscosity modifier, useful for example to inhibit settling or separation of ingredients or to promote redispersibility upon agitation of a liquid composition. In some embodiments, the viscosity modifier is selected from a polymer and a hydrotrope. Optionally, the polymer comprises a block copolymer of propylene oxide and ethylene oxide, for example poloxamers. In some embodiments, the poloxamer comprises poloxamer 407, available under the trade name Pluronic® F127 from BASF Corporation. One or more viscosity modifiers are optionally present in a total amount of 0.01 wt % to 10 wt %, for example 0.1 wt % to 5 wt % or about 0.01 wt % to about 1 wt % of the composition.

Optional ingredients can be present in the personal care composition. Non-limiting examples include skin conditioning agents, moisturizing agents, fragrance, dyes and pigments, titanium dioxide, chelating agents such as EDTA, sunscreen active ingredients such as butyl methoxy benzoylmethane; antiaging compounds such as alpha hydroxy acids, beta hydroxy acids; preservatives such as a mixture of benzisothiazolinone and methylisothiazolinone, glutaraldehyde, sodium bisulfite, hydantoins, imidazolines; polyols such as glycerol, sorbitol, propylene glycol and polyethylene glycols; particulate matter such as silica, talc, or calcium carbonate; antioxidants such as butylated hydroxytoluene (BHT); vitamins such as A, E, K and C; essential oils and extracts thereof such as rosewood and jojoba; particulate matter such as polyethylene beads, jojoba beads, lufa, or oat flour; and mixtures of any of the foregoing components.

In some embodiments, the personal care composition includes fragrance in an amount of about 0.001 wt % to about 2 wt % by weight of the composition.

In some embodiments, the personal care composition includes pearlizers, such as titanium dioxide, in an amount of about 0.01 wt % to 1 wt % by weight.

In some embodiments, the personal care composition includes one or more pigments, such as chromium oxide green, in an amount of about 0.001 wt % to about 1 wt % by weight.

In some embodiments, the personal care composition includes silica, or silicon dioxide, incorporated at a level of from about 0.1 wt % to about 15 wt %, preferable from about 1 wt % to about 10 wt %, more preferably from about 3 wt % to about 7 wt %. Silica is available in a variety of forms, including but not limited to, crystalline, amorphous, fumed, precipitated, gel, and colloidal forms.

In some embodiments, the personal care composition includes inorganic salts, brighteners, perfumes, colorants, sequestering agents, opacifiers, chelating agents (e.g., EDTA), humectants (e.g., polyols, for example, glycerol), or any combination thereof.

In some embodiments, the personal care composition includes free fatty acids to provide enhanced skin feel benefits, such as softer or smoother feeling skin. Suitable free fatty acids include those derived from tallow, coconut oil, palm oil and palm kernel oil.

In another embodiment, the composition of Composition 1, et seq. is a personal care formulation, for example a cleanser such as a liquid hand soap formulation, body wash, or skin cleanser, or a home care formulation, e.g., a hard surface cleanser such as a dish soap, resulting in a concentration gradient of actives and to give a novel aesthetic. In one embodiment, for example, the composition is a hard surface cleanser, e.g., an oil-free and alcohol-free cleanser, e.g., an antimicrobial, oil-free and alcohol-free cleanser.

Any of the compositions of Composition 1, et seq. are suitable for use as cleansers. Typically, skin cleansers will have higher levels of surfactant compared to compositions for oral care use, e.g., anionic surfactants such as sodium laureth sulfate and/or sodium coceth sulfate, e.g., in some embodiments at levels of 5-30%. Dish liquids may have more powerful surfactants, for example amine oxide surfactants, such as lauryl/myristrylamidopropyl dimethylamine oxide In some embodiments, the personal care compositions of Composition 1, et seq. comprise an effective amount of a skin benefit agent, e.g., an antimicrobial agent, e.g., a cationic antimicrobial agent, a moisturizer, and/or a sunscreen. In some embodiments, the skin benefit agent is a cationic active agent, which may provide skin protection benefits, e.g., as moisturizers, and/or may be antimicrobial cationic active agents, for example antimicrobial quaternary ammonium cations (e.g. benzalkonium chloride, cetyl trimethylammonium bromide or chloride, didecyldimethylammonium chloride, cetylpyridinium chloride, benzethonium chloride) and antimicrobial bisguanides (e.g., chlorhexidine digluconate), and combinations thereof, or bisguanides (such as chlorhexidine digluconate), cationic amino acids (such as arginine), metal cations (such as zinc, calcium, or stannous ions), or combinations thereof. Safe and antimicrobially effective levels of cationic active agents a skin care formulation may be significantly higher than the orally acceptable levels for a mouthwash, e.g., by a factor of 10 to 20. For example, antimicrobially effective levels of chlorhexidine in a skin cleanser would in some embodiments be 3-6%, e.g., about 4%. In some embodiments, the personal care compositions of Composition 1, et seq. contain a skin benefit agent which is a sunscreen agent, e.g., p-aminobenzoic acid (PABA), octyldimethyl-PABA, phenylbenzimidazole sulfonic acid, 2-ethoxyethyl p-methoxycinnamate, benzophenone-8, benzophenone-3, homomethyl salicylate, meradimate, octocrylene, octinoxate, octisalate, sulisobenzone, triethanolamine salicylate, avobenzone, ecamsule, titanium dioxide, zinc oxide, or in some embodiments a basic sunscreen agent, for example a triazole or triazine sunscreen, e.g., bisoctrizolem, bisoctrizole, bemotrizinol, tris-biphenyl triazine, drometrizole trisiloxane, ethylhexyl triazone, and the like.

Further provided is a method (Method A) for cleaning and/or protecting the skin comprising shaking the composition according to any of Composition 1, et seq. and washing the skin therewith.

Further provided herein is Method A as follows:

A.1. Method A wherein the composition is any of Composition 1, et seq, e.g., wherein the composition is a liquid hand soap, body wash, make-up remover, or topical disinfectant.

A.2. Method A or A.1 wherein the composition contains 5-35% of a stabilizing surfactant system.

A.3. Any of Methods A, et seq., wherein the composition further comprises a cationic active agent.

A.4. Any of Methods A, et seq., wherein the composition contains an effective amount of an antimicrobial cationic active agent.

A.5. Any of Methods A, et seq., wherein the composition contains an effective amount of a skin-protective cationic active agent, for example to provide a moisturizing and/or sunscreen benefit, or a sunscreen agent.

Further provided is a method (Method B) for cleaning a hard surface, e.g., a dish, kitchenware, or household surfaces, comprising shaking the composition according to any of Composition 1, et seq. and washing the hard surface therewith.

Further provided herein is Method B as follows:

B.1. Method B wherein the composition is any of Composition 1, et seq., e.g., wherein the composition is a dish soap or disinfectant.

B.2. Any of Methods B, et seq., wherein the composition contains 5-35% of a stabilizing surfactant system.

B.3. Any of Methods B, et seq., wherein the composition contains an antimicrobially effective amount of a cationic active agent.

B.4. Any of Methods B, et seq., wherein the method is for the disinfection or disruption of biofilm on a hard surface.

The present disclosure further provides a method (Method C) of cleansing skin or a hard surface comprising the steps of providing a personal care cleansing composition as described above (e.g., any of Composition 1, et seq.); and applying an agitating force to the composition to to provide a cleansing effect.

The present disclosure provides additional exemplary embodiments, including:

C.1. Method C, further comprising the step of agitating the composition sufficiently to create a volume of foam.

Further provided are Compositions 1, et seq. for use in any of Methods A, B or C.

EXAMPLES

Exemplary embodiments of the present disclosure will be illustrated by reference to the following examples, which are included to exemplify, but not to limit the scope of the present disclosure.

In the examples and elsewhere in the description of the invention, chemical symbols and terminology have their usual and customary meanings. Temperatures are in degrees Celsius unless otherwise indicated. The amounts of the components are in weight percents based on the standard described; if no other standard is described then the total weight of the composition is to be inferred. Various names of chemical components include those listed in the CTFA International Cosmetic Ingredient Dictionary (Cosmetics, Toiletry and Fragrance Association, Inc., 7$^{th}$ ed. 1997).

Example 1: Cleansing Composition

Experiments were carried out on dual phase compositions having two clearly defined aqueous phases. Table 1 shows exemplary compositions that were used in the following experiments according to the present disclosure.

TABLE 1

| Biphasic formulation | |
|---|---|
| Component | Concentration (wt. %) |
| Water | q.s. |
| Sodium Laureth Sulfate | 10-20 |
| Tetrasodium N,N-bis(carboxymethyl)-L-glutamate | 0.01-0.1 |
| Benzisothiazolinone/ Methylisothiazolinone mixture | 0.01-0.2 |
| Lauryl/Myristyl Amidopropyl AmineO xide | 5-15 |
| Sodium Bisulfite | 0.001-0.1 |
| Lactic Acid | 0.01-0.1 |
| Poloxamer | 0.1-1 |
| Glutaraldehyde (24% soln.) | 0.001-0.1 |
| Sodium chloride | 0-2 |
| Polyacrylic acid | 10-20 |
| Polyethylene Glycol 8000 | 1-10 |
| Benzophenone-4 | 0-0.1 |
| Magnesium Sulfate Heptaydrate | 0-2 |
| Acticide LG | 0-0.1 |
| Colorants and fragrants | 0.0001-0.1 |

Example 2: Adjustment of Phase Separation

An experiment was carried out to evaluate the effect of a polyacrylic acid polymer, polyethylene glycol (8 kD) and sodium chloride in order to optimize the dual phase dishwashing formula. Several compositions were manufactured varying only the amounts of these three ingredients, and the resulting height of the phases were measured. These materials were evaluated on 2 levels in order to predict its effect. Polyacrylic acid was varied in concentration between 3-7 wt. %, PEG was varied in concentration between 3-7 wt. %, and sodium chloride was varied in concentration between 0.5-3 wt. %. Table 2 displays the results observed.

TABLE 2

| Resulting phase height resulting from variance of certain ingredients | | | | | |
|---|---|---|---|---|---|
| Composition | PEG (wt. %) | Poly acrylic acid (wt. %) | Sodium chloride | BottomPhase height (cm) | Bottom Phase Proportion |
| 1 | 7 | 3 | 3 | 1.0 | 7.7% |
| 2 | 3 | 7 | 0.5 | 2.2 | 17% |
| 3 | 5 | 7 | 3 | 2.0 | 15.4% |
| 4 | 5 | 5 | 1.75 | 2.0 | 15.4% |
| 5 | 3 | 5 | 3 | 1.8 | 13.8% |
| 6 | 7 | 5 | 0.5 | 1.8 | 13.8% |
| 7 | 7 | 7 | 1.75 | 2.0 | 15.4% |
| 8 | 3 | 3 | 1.75 | 0.5 | 3.8% |
| 9 | 5 | 3 | 0.5 | 0.5 | 3.8% |

As shown above in Table 2, the total active ingredient (i.e., the anionic and nonionic surfactant) was set at 14.1 wt. % with a ratio between anionic/non-ionic of 3.5:1. After evaluation, the results were evaluated for the effect of each material on the height of the phases. It was observed that the bottom layer contained substantially all of the polyacrylic acid, while the top layer contained substantially all of the polyethylene glycol. The height of the bottom phase was measured relative to the overall height of the solution, which was 13 cm. Based on these measurements, the percentage of the bottom layer was calculated relative to the total solution height.

Based on analysis with linear regression, this data shows that the polyacrylic acid had the highest impact on the height of the phase separation. From this information, we surprisingly concluded that the polyacrylic acid leads the amount of phase separation. Generally, the more polyacrylate present in the composition, the greater the height of the phase separation will be. It was further observed that the viscosity of the upper layer increases dramatically with the addition of sodium chloride, which indicates that the surfactants typically migrate to the upper layer.

Without being bound to theory, it is believed that inorganic salts, such as sodium salts or magnesium salts, interact with anionic surfactants and affects the viscosity of systems in which they are contained. Thus, if the upper phase changes viscosity with addition of salts, it points toward the anionic surfactants being contained in the upper layer. Based on this hypothesis, the composition was tested to determine the composition of both phases, and it was confirmed that the surfactants are contained in the upper layer, as well PEG 8000 and sodium polyacrylate is contained in bottom layer.

Example 3: Enhanced Foaming Characteristics

A test composition and a control composition were created according to the following formulations, which exhibited a 50%/50% phase ratio:

TABLE 3

Test Formulation and Control Formulation

| Component | Test Formulation | Control Formulation |
|---|---|---|
| Water | q.s. | q.s. |
| Sodium Laureth Sulfate | 12.7 | 12.7 |
| Tetrasodium N,N-bis(carboxymethyl)-L-glutamate | 0.9 | 0.9 |
| Benzisothiazolinone/Methylisothiazolinone mixture | 0.12 | 0.12 |
| Lauryl/Myristyl Amidopropyl Amine Oxide | 7.7 | 7.7 |
| Sodium Bisulfite | 0.015 | 0.015 |
| Pulco 868 Mod | 0.22 | 0.22 |
| Lactic Acid | 0.05 | 0.05 |
| Poloxamer | 0.1 | 0.1 |
| Glutaraldehyde (24% soln.) | 0.03 | 0.03 |
| Sodium chloride | 0.8 | 0.8 |
| Polyacrylic acid | 0 | 16 |
| Polyethylene Glycol 8000 | 0 | 5 |
| Benzophenone-4 | 0.01 | 0.01 |
| Magnesium Sulfate Heptaydrate | 1 | 1 |
| Acticide LG | 0.095 | 0.095 |
| Colorants | 0.001 | 0.001 |

Foam boosting was measured using the Automated Miniplate Dishwashing test, described in U.S. Pat. No. 4,556,509, which yielded the following results. Briefly, the test is used to determine the number of theoretical plates that can be washed in a detergent solution until the foam disappears. This test is used to demonstrate the improvement in cleaning efficiency as gauged by foam volume and foam stability. In the automatic miniplate dishwashing test, the foam is generated in a detergent solution by the action of an agitating brush. The foam is electronically measured by reflectance of the solution surface as mixing soil is added to the detergent solution at a steady rate. The disappearance of the foam determines the endpoint of the test, and the number of mini plates is then calculated based on foam duration and the rate of soil addition.

The test was carried out using sodium polyacrylic acid at a concentration of 16 wt. % and a binary system of surfactants (i.e., sodium laureth sulfate and lauryl/myristyl amidopropyl amine oxide), the performance was compared with a control formula without sodium polyacrylate.

TABLE 4

Foam test results

| Test Run | Composition | Miniplates Cleaned |
|---|---|---|
| Test 1 | Control | 15.88 |
|  | Formulation with Sodium Acrylate polymer | 24.46 |
| Test 2 | Control | 19.16 |
|  | Formulation with Sodium Acrylate polymer | 22.68 |
| Test 3 | Control | 16.43 |
|  | Formulation with Sodium Acrylate polymer | 26.47 |

As shown, in each instance the test compositions containing the sodium acrylate polymer had superior results in comparison with the control composition. On average, the test formulation showed a 43% improvement in cleansing ability. Analysis of the results showed that this difference achieves statistical significance ($p=0.016$).

What is claimed is:

1. A cleansing composition comprising an aqueous solution of:
   an anionic polymer;
   a nonionic polymer; and
   a phase-stabilizing amount of surfactants comprising a combination of at least one anionic surfactant and at least one nonionic surfactant, wherein the nonionic surfactant comprises a C8-C22 tertiary amine oxide or a fatty acid amide;
   wherein the solution comprises two distinct aqueous phases having different composition and density, the two distinct phases comprising all of one of the anionic polymer or the nonionic polymer;
   wherein the nonionic polymer comprises polyethylene glycol having a molecular weight of 5kD to 10kD in an amount of 0.1-10 wt. % of the composition;
   wherein the anionic polymer is an acidic polymer selected from a polyacrylate made of homopolymers or co-polymers of a combination of acrylic acid derivatives or a synthetic anionic linear polycarboxylate; and
   wherein the acidic polymer is present in an amount of 5-25 wt. % of the composition.

2. The cleansing composition according to claim 1, wherein the anionic surfactant comprises a hydrophobic group that is a C8-C22 alkyl or acyl and a water-solubilizing group selected from sulfonate, sulfate, and carboxylate.

3. The cleansing composition according to claim 1, wherein the anionic surfactant is sodium laurel ether sulfate, sodium lauryl sulfate, ammonium lauryl sulfate, a sodium alkyl benzene sulfonate, or magnesium alkyl benzene sulfonate.

4. The cleansing composition according to claim 1, wherein the anionic surfactant is sodium laurel ether sulfate.

5. The cleansing composition according to claim 1, wherein the nonionic surfactant comprises at least one of laurylamidopropyl amine oxide, myristylamidopropyl amine oxide, cocomonoethanolamide, or combinations thereof.

6. The cleansing composition according to claim 1, wherein the nonionic surfactant is a combination of laurylamidopropyl amine oxide, myristylamidopropyl amine oxide.

7. The cleansing composition according to claim 1, wherein the ratio of anionic surfactant to nonionic surfactant is about 1:1 to about 1:3.5.

8. The cleansing composition according to claim 1, wherein the acidic polymer is a homopolymer of polyacrylic acid.

9. The cleansing composition according to claim 1, wherein the acidic polymer is present in an amount of about 5-25 wt. %, about 8-22 wt. %, about 10-20 wt. %, about 13-18 wt. %, about 15-17 wt. %, or about 16 wt. % of the composition.

10. The cleansing composition according to claim 1, wherein the polyethylene glycol has a molecular weight of.

11. The cleansing composition according to claim 1, wherein the nonionic polymer is present in an amount of about 2-8 wt. %, 4-6 wt. %, or about 5 wt. % of the composition.

12. The cleansing composition according to claim 1, wherein the composition is a cosmetic product, cosmetic-removal product, deodorant or antiperspirant product, hair care product, shaving product, sun bathing product, insect repellent product, skin care product or personal cleansing product, a liquid hand soap, shower gel, body wash, bath foam, shampoo, liquid face soap, dish soap, body wash, dermal cream, or liquid laundry detergent, or liquid detergent for cleaning hard surfaces.

13. The cleansing composition according to claim 1, wherein the composition is a cream, lotion or gel for the skin.

14. The cleansing composition according to claim 1, wherein the composition is a liquid hand soap, dish soap, liquid laundry detergent, or liquid detergent for cleaning hard surfaces.

15. The cleansing composition according to claim 1, comprising:
  a) an acidic polymer selected from one or more of (a) acrylate homopolymers or co-polymers of a combination of acrylic acid derivatives, and (b) synthetic anionic linear polycarboxylates, wherein the acidic polymer is present in an amount of 5-25 wt. % of the composition;
  b) a nonionic polymer comprising polyethylene glycol having a molecular weight of 5kD to 10kD in an amount of 0.1-10 wt. % of the composition;
  c) a phase-stabilizing amount of surfactants comprising a combination of at least one anionic surfactant and at least one nonionic surfactant, wherein the anionic surfactant comprises a hydrophobic group that is a C8-C22 alkyl or acyl and a water-solubilizing group selected from sulfonate, sulfate, and carboxylate, and wherein the nonionic surfactant comprises a C8-C22 tertiary amine oxide or a fatty acid amide;
  wherein the solution comprises two distinct aqueous phases having different composition and density, the two distinct phases comprising all of one of the anionic polymer or the nonionic polymer.

16. A method of cleansing and/or protecting the skin, or cleaning a hard surface, e.g., a dish, kitchenware, or household surfaces, comprising shaking the cleansing composition according to claim 1 and washing the skin or the hard surface therewith.

17. The method according to claim 16, further comprising the step of agitating the cleansing composition to create a volume of foam.

* * * * *